United States Patent [19]

Bevilacqua

[11] 4,063,352

[45] Dec. 20, 1977

[54] METHOD OF MAKING ELECTRODE PACKAGE

[75] Inventor: Albert J. Bevilacqua, Downers Grove, Ill.

[73] Assignee: M I Systems, Inc., Westmont, Ill.

[21] Appl. No.: 752,678

[22] Filed: Dec. 20, 1976

Related U.S. Application Data

[62] Division of Ser. No. 706,012, July 16, 1976, Pat. No. 4,034,854.

[51] Int. Cl.² ............................................. H01R 9/02
[52] U.S. Cl. ........................................ 29/630 R; 29/624;
128/417; 128/DIG. 4; 156/226; 156/252;
156/291; 156/293
[58] Field of Search ................. 29/624, 630 R, 430;
156/252, 226, 291, 293; 128/2.06 E, 2.1 E, 404,
416, 417, 418, DIG. 4; 206/210, 328, 329, 332,
363, 370, 372, 438, 462, 485, 445

[56] References Cited

U.S. PATENT DOCUMENTS

| | | | |
|---|---|---|---|
| 2,676,704 | 4/1954 | Marks | 156/252 X |
| 3,602,216 | 8/1971 | Moe, Jr. | 128/417 X |
| 3,701,346 | 10/1972 | Patrick, Jr. et al. | 206/328 X |
| 3,805,769 | 4/1974 | Sessions | 29/630 R X |
| 3,820,531 | 6/1974 | Szpur | 128/417 X |
| 3,828,766 | 8/1974 | Krasnow | 128/417 X |
| 3,989,035 | 11/1976 | Zuehlsdorff | 128/DIG. 4 X |

*Primary Examiner*—Victor A. DiPalma
*Attorney, Agent, or Firm*—Olson, Trexler, Wolters, Bushnell & Fosse, Ltd.

[57] ABSTRACT

There is disclosed a novel electrode assembly or package for two or more electrode devices, and also a novel method of fabricating not only the overall assembly, but also the devices in conjunction therewith. The electrode assembly as contemplated by the disclosure includes a carrier member in generally strip form having one or more openings therein, the number of said openings depending upon and being equal to one-half of the number of electrode devices to be employed in said assembly. A medical electrode device is secured in overlying relation to each opening, on opposite sides of the carrier member, with the gel pads of each said electrode device being disposed within the periphery of the opening and in face-to-face contact with the pad of the opposed electrode device. The electrode devices may be pre-gelled, if desired. It is contemplated that the assembly may then be packaged in a suitable container, such as a plastic or foil envelope. The method as disclosed involves the fabrication of the electrode device in an assembled relation with a carrier strip so as to provide a length of strip material having a plurality of said devices secured thereto, and the subsequent folding over of said strip to provide a carrier member with electrode devices on opposite sides thereof.

9 Claims, 7 Drawing Figures

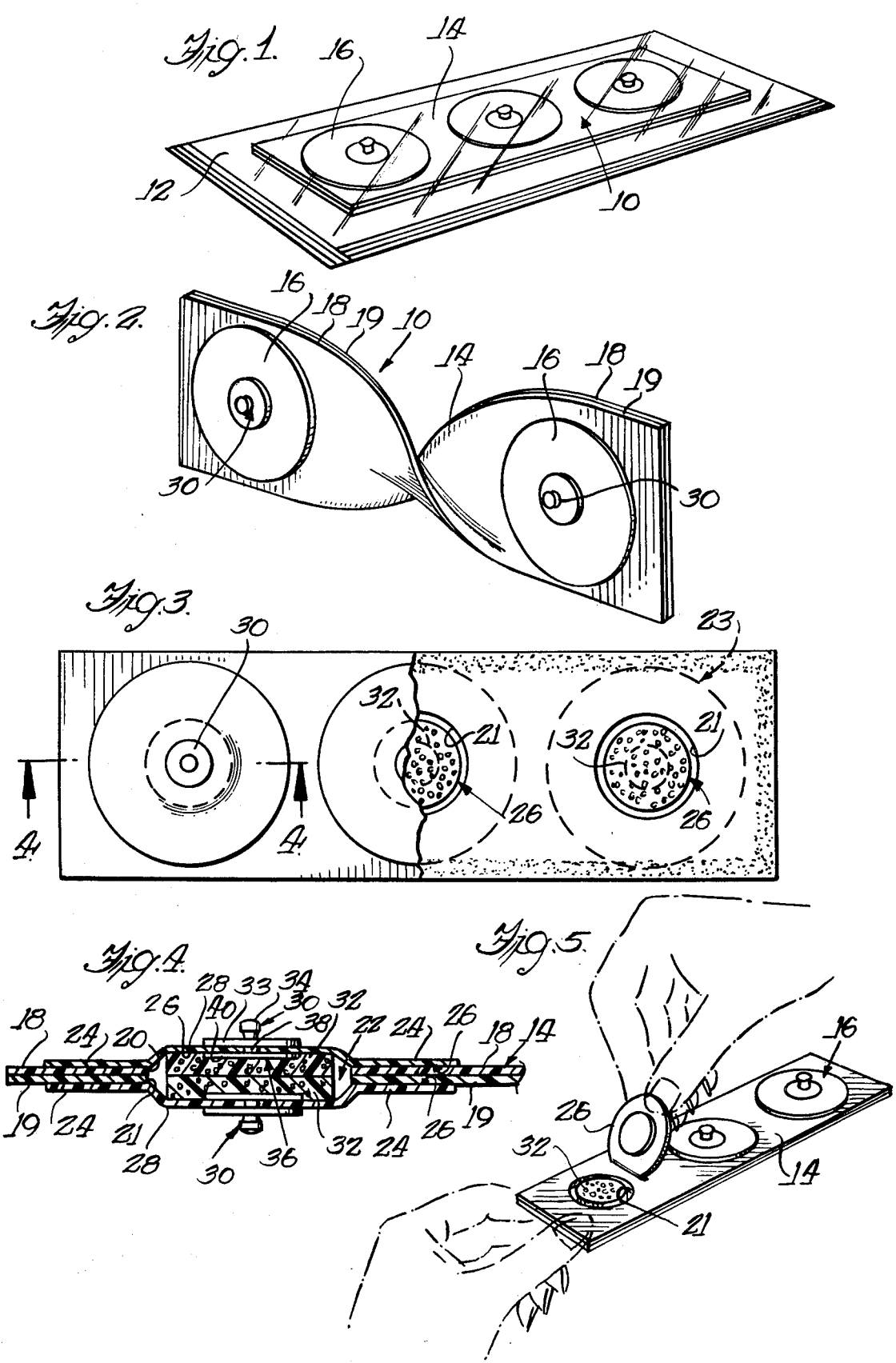

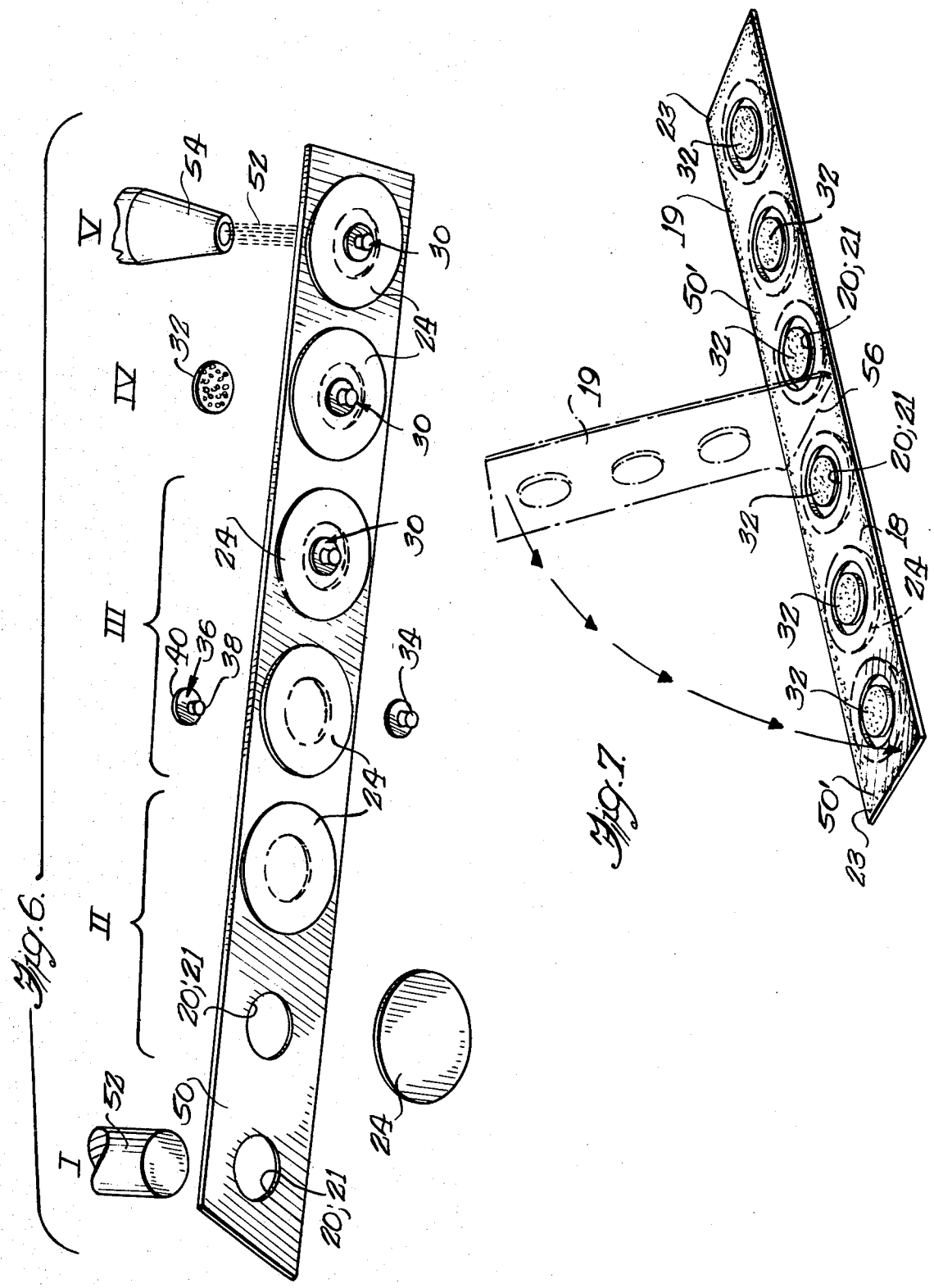

METHOD OF MAKING ELECTRODE PACKAGE

REFERENCE TO RELATED APPLICATION

This application is a division of U.S. patent application Ser. No. 706,012, filed July 16, 1976, now U.S. Pat. No. 4,034,854.

BACKGROUND OF THE INVENTION

The present invention relates to electrode devices such as are used in EKG procedures, and more specifically to a novel assembly or package for said devices, and a novel method of manufacture of said assembly and said electrode devices.

With regard to the health care field, it is relatively common place today to employ the monitoring of human body functions as part of surgical procedures, and also for other testing and diagnostic purposes. One of the more common monitoring procedures (referred to as "ECG") is the use of electrode devices which are attached to the skin surface of a patient and when connected to appropriate monitoring and recording apparatus will provide both a visual and/or graphic representation as to the function of the patient's heart.

The electrode devices used in the above-mentioned ECG procedure normally include an electrical contact element which in conjunction with an electrical conductive gel applied to the skin of the patient, enables the monitoring apparatus to pick up a reading related to the bio-skin potential of the patient. This potential not only is detected, but is generally recorded both in visual and graphic form. ECG electrode devices to perform this function are well known in the art, and by way of example, two types thereof are shown in the U.S. Pat. Nos. 3,805,769 and 3,828,766.

The medical profession and the public in general has become extremely conscious of the need to monitor the heart of a patient, whether in surgery, for diagnostic purposes, or pursuant to an emergency situation resulting from a cardiac arrest or the like. In this regard almost all surgical procedures involve the monitoring of the patient; para-medic teams often will employ portable ECG monitors to transmit readings to a remote hospital so that they can be advised as to the manner in which to treat emergency heart-attack victims; hospitals have established coronary care and intensive care units, wherein the patients heart and other body functions are monitored on a continuous basis. All of this has led to a great demand for electrode devices which are efficient, convenient to use, and in many instances pre-gelled and disposable. Of course, an additional extremely and important factor is the ultimate cost of the electrodes.

The present invention as will be detailed hereinafter, provides a pre-gelled electrode assembly or package, and a method of manufacture thereof, which permit the efficient and economical fabrication of the electrode, without sacrificing quality or performance. The specifics of said method and structure will become more apparent from the description of the drawings and the discussion of the illustrated embodiment shown therein, both of which follow hereinafter.

DESCRIPTION OF THE DRAWINGS

FIG. 1 is a perspective view of an electrode package of the present invention, housed within a clear envelope.

FIG. 2 is a perspective view of an assembly constructed in accordance with the present invention, with one portion thereof twisted approximately 180° to illustrate the fact that the electrode devices are mounted on both sides of the carrier strip.

FIG. 3 is a top-plan view of an assembly according to the present invention, such as shown in FIG. 1, with a portion of the upper carrier member layer removed.

FIG. 4 is a partial sectional view of the assembly of the present invention taken along the line 4—4 of FIG. 3.

FIG. 5 is a perspective view illustrating the manner in which an electrode device is removed from the assembly.

FIG. 6 is a schematic representation of the initial steps performed in a preferred method of fabrication of the assembly of the present invention.

FIG. 7 is a perspective view of a strip of carrier material, having a number of electrodes applied, and illustrating in phantom how said strip is folded over upon itself to provide the completed assembly with electrode devices on opposite sides of the carrier member.

DESCRIPTION OF THE ILLUSTRATED EMBODIMENT OF THE INVENTION

As discussed above, the present invention concerns not only the basic electrode package or assembly, but also the general method of fabrication, in addition to a specific, preferred method, wherein the fabrication steps are performed in sequence on a continuous length of strip material. In this regard, the electrode assembly of the present invention is shown in FIG. 1-5, with the above-mentioned preferred form of the method of fabrication being illustrated schematically in FIGS. 6 and 7. Initially, the structure of the electrode package will be considered, with a discussion of the method of fabrication being presented thereafter.

Electrode Assembly Structure

Referring initially to FIG. 1, there is shown an electrode assembly fabricated in accordance with the present invention, and designated generally 10. The assembly 10 is housed or contained in a clear plastic envelope 12. While the package 10, per se, provides a significant barrier against disipation of the gel, placement of the package 10 within the sealed envelope 12 provides an added degree of protection and tends to prolong the overall shelf life of the assembly. The envelope 12 may be of clear plastic as shown, or may be made of metalized foil or any other desired material which will provide a barrier against dissipation of the gel.

The assembly 10 includes an elongate carrier member 14 which is in generally stripped form, said member 14 having electrode devices 16 secured to the opposite sides thereof, as shown in FIG. 2. Of course, the number of electrode devices 16 to be employed and the length of carrier member 14 may be varied as needed.

The basic construction of the assembly 10, and the individual electrode devices 16 can best be understood with reference to FIG. 4, and attention is directed thereto. In this regard, the carrier member 14 of the embodiment as shown, is of a double layer or two-ply thickness, as provided by an upper layer 18 and a lower layer 19 which are joined together in generally face-to-face contact. Both upper layer 18 and lower layer 19 are provided with apertures 20 and 21, respectively, which in the assembled condition are in generally coaxial alignment and cooperate to define an opening 22 in the carrier member 14.

The electrode devices 16 are secured to the opposite surfaces of the carrier member 14, defined respectively by layers 18 and 19, said devices 16 disposed in overlying relation to the aforementioned opening 22. As mentioned above, respective layers 18 and 19 are secured together in face-to-face engagement, which may be accomplished by use of an adhesive 23 or the like applied along the peripheral edges of said layers as shown in FIG. 3.

The construction of the electrode devices 16 can best be understood from FIG. 4, keeping in mind that said devices are of identical construction. That is to say, each device 16 includes a base section or layer 24 having an adhesively-coated inner surface 26 in engagement with the carrier member 14, and a non-adhesive, outer surface 28. An electrical connector 30 is secured to the base section 24 which in the illustrative device is in the form of a conventional snap-type fastener. A pad 32 of porous or foam-type material is engaged with the adhesive surface 26 in overlying relation to the inner portion of the connector 30 and generally within the perimeter of the opening 22. In the assembled condition of the illustrated embodiment each of the pads 32 will have a quantity of electro-conductive gel (no reference character) pre-applied thereto.

As mentioned previously, the electrical-connector 30 is of a conventional design, and more specifically is in the nature of a snap-type fastener such as sold by the Dot Fastener Division of TRW. More specifically, connector 30 is of a two-piece construction, with the respective elements thereof being mechanically joined to provide an integral unit. In this regard, with reference to FIG. 4, there is provided an outer element 33 having a stud 34 to which a lead wire (not shown) of a monitoring apparatus may be connected. The inner element of the connector 30 is designated generally 36, and includes a post 38 which extends through the base section 24 and is mechanically joined to the outer connector element 33. In the preferred embodiment, the inner connector element 36 includes a rather broad contact portion or surface 40 which is overlapped by the gel pad 32. The surface portion 40 is smaller than the opening 22 in the carrier member 14. Accordingly, upon assembly of connector 30 there will exist an exposed, generally annular surface area of the adhesively-coated surface 26 of base member 24. Pad 32 is secured to this exposed area, as will be discussed in more detail hereinafter.

As can be seen in FIG. 4, the gel pads 32 of the respective electrode devices 16 are disposed within the periphery of the opening 22 in carrier member 14. Carrier member 14 and the respective base sections 24 thus in effect define an enclosed, sealed area or chamber for the pads 32, which tends to prevent premature, undesired drying out or disipation of the gel material applied to said pads. As an additional matter, the assembly of the present invention has been designed such that the pads 32 are in face-to-face abutting contact. It has been found that in this disposition the pre-gelled pads tend to compliment each other and contribute toward a better more dependable product. More specifically provides an increased volume for the gel material and assures that both pads will contain the required quantity. Also, upon removal, the pads 32 can not adhere to any surface, which adhesion could result in the pads 32 being pulled loose. This latter problem is often encountered in prior art type devices wherein a separate cover member is employed over the gelled pad.

Depending, of course, upon the intended use, the thickness of the carrier member 14 can be varied to provide an increased volume for the pre-gelled pads 32 so as to permit the addition of a larger quantity of gel. This increased volume will preclude the pads from being overly compressed during transport or storage.

Once it is desired to utilize the assembly of the present invention, the seal on the envelope 12 is broken and the assembly 10 removed. Next, an individual electrode device is peeled from the carrier member 14 and applied to the skin surface of a patient. It is to be understood, that the composition of the carrier member 14 is such that the surface thereof to which devices 16 are attached will permit easy release of said devices, as is well known in the pressure sensitive art. Once the devices 16 have been removed from the carrier strip and placed upon the skin surface of a patient, lead wires from monitoring apparatus can then be connected to the electrical connector 30 as desired.

Method of Fabrication

Attention is now directed to FIG. 6 and 7, wherein there is disclosed a preferred method for fabricating the electrode devices 16 and the assembly 10 as described above, and illustrated with respect to FIGS. 1–5. In this regard, it should be noted that the method of the present invention is illustrated schematically with regard to the various steps to be performed. As will be discussed more fully hereinafter, the apparatus contemplated for performance of the steps of the method is all well known in the art, and while the same will be mentioned hereinafter, a detailed illustration and discussion thereof has not been provided, as same is not deemed unnecessary to a complete understanding of the invention, and would only serve to prolong and confuse the specification. As a further point, it should be kept in mind that a preferred form of method of fabrication involves the sequencial formation of the electrode devices on a continuous strip 50 of carrier material is illustrated. The basic steps of the method, however, need not be performed in sequence, or in the sequence as illustrated in the drawings.

Looking initially to FIG. 6, a continuous length of carrier material 50 is provided, which material would be stored in roll form (not shown) and delivered from said roll to the various stations I–V as illustrated and discussed hereinafter. It is contemplated that the steps of the present invention will be performed by use of a machine which employs an intermitent drive mechanism for indexing the strip 50 sequencially between the respective stations I–V. In this regard, the steps of the method to be described hereinafter will be performed sequencially and simultaneously at the various stations: i.e. at the time the operation at Station I is being performed at one location along the strip, the operation at Stations II, III, IV and V will be performed at other locations along the strip. Thus, upon each indexing of the drive mechanism, the strip will be moved forward and a completed electrode device will pass the exit portion of the machine.

Looking now to FIG. 6, at Station I, the punch 52 or some other conventional device is employed to form an aperture in the strip material 50. The aperture thus formed is designated 20,21; as said apertures will eventually, upon final assembly, define the opening 22, as will become apparent from the following discussion. Of course, a pre-punched length of strip material may be used, if desired.

Once the aperture 20,21 has been formed, the strip material is indexed to Station II, wherein the base section 24 is applied to the lower surface of said strip 50, as viewed, in overlying relation to the aperture 20,21. The base section 24 is shown in the form of a disc, however, any desired shape may be employed. The operation of applying the base section 24 to the strip 50 wherein simultaneous, sequential operation is to be employed is by use of conventional automatic label applying apparatus such as sold by the Avery Label Company, and is well known in the art. While employment of the automatic applicating apparatus is preferred and contemplated, base section 24 could be applied by less automated procedures, or by hand.

The strip of material 50, with the base section 24 is overlying relation to the aperture 20,21 is then moved or indexed to Station III, wherein the electrical connector 30 is applied. Recalling the prior discussion concerning the connector 30, it will be recalled that said connector is comprised of two separate elements 34 and 36 which are mechanically joined together, with the post 38 of the element 36 extending through the base section 24 and being cold formed to assembled relation with the outer connector element 34. Here again, this operation may be employed by manually operated devices, or by automatic snap fastener applicator units, both of which are well known in the art and can be obtained from the manufacturers of the snap fastener devices.

The next step in the fabrication of the assembly 10 and construction of the device 16 of the present invention, involves the mounting of the pad 32. In this regard, it should be noted that pursuant to the assembly of the connector 30 at Station III, the contact portion 40 of the inner connector element 36 is sized such that same is somewhat smaller than the aperture 20,21 thereby leaving an exposed generally annular area of adhesively-coated surface 26 between the periphery of the aperture 20,21 and the perimeter of the contact portion 40. In this regard, the pad 34 is brought into contact with said exposed area with the adhesive surface 26 securing the pad 32 to the base section 24. Here again, conventional cutting dyes and punches may be employed to cut the pad 32 from a strip of foam material and to apply said pad 32 against the exposed area of the adhesive surface 26.

Once the pad 32 has been applied, the next indexing of the drive mechanism will bring the strip material 30 into alignment with Station V. Assuming a pre-gelled assembly 10, at said Station V, a nozel 52 is provided, which automatically dispenses a pre-determined quantity of gel 52 onto the pad 32. Of course, if a non-gelled arrangement is desired, as is contemplated, the application step at Station V is omitted.

From the above discussion, it can be seen that as the drive mechanism for the strip material 50 indexes, each instance of index thereof, will move a section of strip material 50 past the respective Stations I-V and also past the discharge end of the machine. Accordingly, there is provided a continuous strip of material 50 having the electrode devices 16 formed thereon.

The next step in the method of fabrication of the assembly 10, is shown in FIG. 7. This step involves the severing from said continuous strip 50, of a section of carrier material 50, having a pre-determined number of electrode devices 16 mounted thereon. The severed section 50 is folded about a fold line 56 proximate the middle section thereof, i.e. assuming employment of six electrode devices, proximate the third and fourth such device, as illustrated in phantom in FIG. 7. The respective strip portions defined upon the folding of the severed section 50 about the fold line 56 are designated generally by reference characters 18 and 19, since these strip portions conform to and provide the layers 18 and 19 discussed above. The folding operation proceeds to such an extent, that the respective strip portions 18 and 19 are brought into surface-to-surface engagement, with the apertures 20,21 being aligned and defining the opening 22 in the carrier member 14. Also, the pads 32 of the opposed electrodes 16 are brought into abutting face-to-face engagement, as is clearly illustrated in FIGS. 3 and 4. Once the portions 18 and 19 are so engaged, they are then secured along the peripheral edges thereof. This step in the illustrated embodiment is achieved by employment of the adhesive 23.

As to the adhesive 23, this may take many forms. That is to say, the adhesive may be of the dry, heat activated type applied to strip material 50 prior to fabrication of the electrode devices 16; or the adhesive may be applied at a station on the aforementioned machines; or merely applied manually. Also other methods of joining the layers or strip portions 18 and 19 are contemplated, for example, ultra sonic welding, or heat sealing may be employed.

There thus has been disclosed a novel multiple electrode package device and method of fabrication, which method includes a novel procedure for the formation of an electrode device. The preceeding discussion and description has been set forth with respect to a preferred method and electrode construction. It is envisioned that those skilled in the art, and armed with the present disclosure may desire various changes or alternate steps or design, in an attempt to avoid the hereinafter claims many of which have been contemplated by the applicant.

Insofar as said changes, alterations, etc. fall with the claims appended hereto, they also fall within the spirt and scope of the invention, as defined by said claims.

The invention is claimed as follows:

1. A method of fabricating an electrode package having a carrier member with at least one opening formed therein, and at least two electrode devices secured to said carrier member, one said device being secured to one surface thereof and the other to the opposite surface thereof, both in overlying relation to said opening, said method comprising the steps of:
 providing a length of apertured carrier material in strip form having at least two apertures formed therein;
 providing at least two electrode devices secured to a first surface of said strip of carrier material in overlying relation to said apertures;
 folding said length of strip material along a fold line proximate the midpoint thereof, such that two separate portions are defined of generally equal length;
 bringing said portions into engagement along a second surface of said strip of carrier material with said apertures in generally coaxial alignment;
 securing said portions of the strip material together along said second surface thereof such that said said portions in effect define a multiple-layer carrier member, with said pair of aligned apertures in effect defining a single opening in the said carrier member.

2. A method of manufacturing a pre-gelled, multiple electrode assembly, which assembly comprises a carrier member having at least one opening formed therein, with electrode devices secured to opposite sides of said carrier member in overlying relation to said opening, said method comprising the steps of: providing a section of carrier material in strip form having at least two apertures formed therein; applying a base member having an adhesively-coated surface to said strip in overlying relation to each said aperture, with said adhesively-coated surface engaging said strip; mounting an electrical connector to each said base member with a contact portion thereof on said side corresponding to said adhesively-coated surface, and disposed within the periphery of said aperture, so as to provide an exposed annular area of adhesively-coated surface defined by the periphery of said aperture and said contact surface; applying a pad in overlying relation to said contact surface by engaging said pad to said exposed adhesively-coated annular area of each said base section; applying a quantity of electroconductive gel to each said pad; folding said section of carrier material along a fold line intermediate said apertures to define a pair of respective strip portions, and bringing said strip portions into surface-to-surface contact, with said apertures in generally co-axial alignment and said gelled pads into abutting face-to-face relations; securing said strip portions together along the peripherial edges thereof such that there is provided a double-layer carrier member with electrode devices secured to the opposite surfaces thereof, with said aligned apertures in effect providing a single opening in the resulting carrier member.

3. A method according to claim 2, wherein said strip is provided with six apertures, and said step of folding the section of carrier material involves employment of a fold line disposed between the third and fourth apertures thereof.

4. A method according to claim 2, further including the step of providing an adhesive or cohesive substance along the edges of said section of carrier material, such that upon the step of folding said section to bring the respective strip portions in face-to-face relation, said portions will be secured together by said substance.

5. A method according to claim 4 wherein said adhesive substance is applied to said carrier section subsequent to the formation of said electrode devices.

6. A method according to claim 4, wherein said substance is applied to said carrier section prior to the formation of said electrode devices.

7. A method according to claim 2, wherein the step of providing a section of carrier material having apertures formed therein, includes the steps of; providing a continuous length of carrier material in strip form, punching holes in said length of carrier material at predetermined locations; said method further including the steps of moving said punched carrier material to a series of stations in sequence, wherein the base material is applied, the electrical connector is mounted, and the pad affixed and the gel material applied, severing said continuous strip, after a predetermined number of electrode devices have been formed to provide a section thereof containing the desired number of electrode devices prior to said steps of folding said section and the securing of the resulting portions thereof.

8. A method of fabricating an electrode package having a carrier member with at least one opening formed therein, and at least two electrode devices secured to said carrier member, one said device being secured to one surface thereof and the other to the opposite surface thereof, both in overlying relation to said opening, said method comprising the steps of:

providing a continuous length of carrier material in strip form:

moving a section of said strip material to a first station wherein an aperture is formed therein; moving said section of strip material to a second station and applying a section of base material in overlying relation to said aperture formed at said first station;

moving said section of strip material to a third station and mounting an electrical connector to said section of base material, applied at said second station;

moving said section of strip material to a fourth station and engaging a porous pad to said adhesively-coated surface, which step includes positioning said pad within the periphery of said aperture formed in said section of strip material;

moving said section of said strip material to a fifth station and applying a quantity of electro-conductive gel to said pad;

performing the operation at said respective stations in sequence, such that said continuous length of carrier material is provided with a plurality of electrode devices mounted thereon;

severing said continuous length of material to provide a section of strip material having a desired, even number of electrodes thereon;

folding said severed section of strip material along a fold line proximate the midpoint thereof, such that two separate strip portions are defined of generally equal length and bringing said portions into surface-to-surface engagement with the apertures therein and generally co-axial alignment and said pads in face-to-face engagement;

securing said strip portions together along the peripheral edges thereof such that said portions in effect define a multiple layer carrier number, with each pair of aligned apertures in effect defining a single opening in the said carrier member.

9. A method according to claim 8, further including the step of applying a quantity of conductive gel to said pads prior to the step of folding the strip material to bring the respective carrier section portions into surface-to-surface engagement.

* * * * *